United States Patent
Kumabe

[11] Patent Number: 6,159,504
[45] Date of Patent: Dec. 12, 2000

[54] CORE SUBSTANCE-CONTAINING CALCIUM MICROPARTICLES AND METHODS FOR PRODUCING THE SAME

[75] Inventor: Kiyoshi Kumabe, Chiba, Japan

[73] Assignee: Kitii Corporation, Ltd., Japan

[21] Appl. No.: 09/228,289

[22] Filed: Jan. 11, 1999

[51] Int. Cl.[7] ........................................... A61K 9/14
[52] U.S. Cl. ................................................ 424/489
[58] Field of Search ............................... 424/489

[56] References Cited

U.S. PATENT DOCUMENTS 5,648,097   7/1997   Nuwayser ............................. 424/489

FOREIGN PATENT DOCUMENTS 04217625   8/1992   Japan .
07328416   12/1995   Japan .

Primary Examiner—Shelley A. Dodson
Assistant Examiner—Konata M. George
Attorney, Agent, or Firm—Finnegan, Henderson, Farabow, Garrett & Dunner, L.L.P.

[57] ABSTRACT

It is an object of the invention to provide core substance-containing calcium microparticles and methods for producing them.

As means to solve the above problem, an edible oil, a calcium shell-forming material and water are agitated at a high rate to thereby form an o/w emulsion and, at the same time, allow electrostatic adsorption of calcium microparticles on the surface of oil droplets in the emulsion; the calcium microparticles adsorbed on the oil droplets are solidified to allow formation of calcium shells; the resultant edible-oil-containing calcium shells are separated; the edible oil is replaced with a solvent; the solvent is removed by volatilization to thereby obtain porous, hollow calcium shells; a core substance is introduced into the porous, hollow calcium shells; and, if necessary, the resultant core substance-containing calcium microparticles are coated with a biopolymer.

The present invention has made it possible to select, as a core substance, not only an oily substance or oil-soluble substance but also a water-soluble substance, suspension or microorganism. Furthermore, if the calcium microparticles of the invention are coated with a biopolymer, a function depending on the property of the polymer, e.g. taste or odor-masking property or slow release property, can be conferred.

11 Claims, No Drawings

CORE SUBSTANCE-CONTAINING CALCIUM MICROPARTICLES AND METHODS FOR PRODUCING THE SAME

BACKGROUND OF THE INVENTION

The present invention relates to core substance-containing calcium microparticles and methods for producing the microparticles.

As a core substance to be enclosed by the method of the invention, any substance may be selected. For example, the core substance may be one of table luxuries, seasonings, flavoring agents, vitamins, drugs, antibiotics, physiologically active substances, or microorganisms. Thus, the present invention can be used in various fields such as the food industry and pharmaceutical industry.

In drugs and a group of foods called "health foods" (e.g. functional foods from natural sources), some of them are physically and/or chemically unstable; some of them have a bitter taste or offensive smell; and some of them are easily degraded in the stomach.

As a method for stabilizing such substances during storage or in the digestive tract and facilitating oral administration of drugs or health foods with a bitter taste or offensive smell, various means have been employed including enclosure into capsules, combination of flavoring/aromatic agents, and various coatings (sugar coating, enteric coating, etc.). However, since capsules and coated tablets are relatively big in size, some individuals feel difficulty in taking them; they are not absorbed well; and it is difficult to use them as a raw material for preparing processed food.

Toward the solution of the above problems, the present inventors have found that it is possible to enclose an oily physiologically active substance with solid microparticles by utilizing the following principle. Briefly, when an oily physiologically active substance is added to water and agitated at a high rate to form an o/w emulsion, the oil droplets in the emulsion behave as a sort of solid; as a result of relative movement with the water, $\zeta$ potential is generated on the surface of the oil droplets and they are electrostatically charged; under this state, if solid microparticles are added which are smaller than the oil droplets and which bring about an electric charge opposite to that on the oil droplet surface, the solid microparticles are adsorbed on the oil droplet surface. Also, the inventors have found that calcium particles are preferable as the solid microparticles. Thus, the inventors have already filed a patent application for the above findings (Japanese Unexamined Patent Publication No. 7-328416).

However, if the core substance of the microparticles is unstable, sometimes the inherent properties of the core substance may change due to temperature, pH, agitation rate and the passage of time. Thus, the selection of the core substance was restricted. When the core substance is water-soluble, the substance easily elutes into the water phase during the manufacturing process, causing a problem that its enclosure is extremely difficult or impossible.

Further, although the oily physiologically active substance-enclosing microparticles disclosed in Japanese Unexamined Patent Publication No. 7-328416 mentioned above have acid resistance, they do not have a function to regulate the dissolution rate of the core substance. Thus, it was difficult to apply those microparticles to drugs and the like which are required to maintain their efficacy in the body for a long period of time.

SUMMARY OF THE INVENTION

It is the major object of the invention to provide calcium microparticles which can enclose as a core substance not only an oily or oil-soluble substance but also a water-soluble substance, suspension or microorganism that has been extremely difficult or impossible to enclose, and a method for producing the microparticles.

It is an additional but important object of the invention to provide such calcium microparticles that, for example, mask the smell or bitter taste of the core substance; increase the storage life of the core substance; make the core substance pH sensitive; or give slow release property to the core substance so that the core substance can function for various purposes, as well as a method for producing such microparticles.

According to the present invention, the major object described above can be achieved by a method for producing core substance-containing calcium microparticles, comprising a step of adding an edible oil and a calcium shell-forming material into water, forming an o/w emulsion by agitating the mixture at a high rate, allowing the static electricity generated by friction between oil droplets and water droplets in the emulsion to form calcium shells on the surface of the oil droplets and allowing the calcium shells to solidify; a step of separating solid matters from the resultant mixture by centrifugation or filtration and drying the solid matters to thereby obtain edible oil-containing calcium shells; a step of replacing the edible oil contained in the calcium shells with an alcohol or a polar solvent and drying the calcium shells to thereby generate porous, hollow calcium shells; a step of adding the hollow calcium shells to a core substance solution or suspension separately prepared and introducing the core substance into the hollow calcium shells under reduced pressure; and a step of drying the resultant core substance-containing calcium shells.

The additional object described above can be achieved by the above method for preparing core substance-containing calcium microparticles further comprising a step of coating the core substance-containing calcium shells with a biopolymer.

According to the present invention, various substances may be used as the core substance, and various functions depending on the purpose of use may be rendered on the core substance.

DESCRIPTION OF THE PREFERRED EMBODIMENT

As the calcium shell-forming material, one or more substances selected from milk calcium, inorganic calcium and organic calcium may be used. The calcium shells may be prepared by the following manner.

When milk calcium is used as the calcium shell-forming material, an edible oil and milk calcium powder are added to water and agitated at a high rate to form an o/w emulsion and, at the same time, electrostatically adsorb calcium microparticles around oil droplets. Then, the calcium microparticles gradually stick to form calcium shells. (Since a commercial milk calcium contains milk protein by several percent, stable calcium shells are formed without addition of a sticking agent.) Subsequently, the resultant solution containing the calcium shells are spray-dried to thereby obtain edible oil-containing calcium microparticles. The conditions of the above agitation are at 9,000 rpm and for about 10 min.

When inorganic calcium such as calcium carbonate is used as the calcium shell-forming material, an edible oil and a calcium salt powder are added to water and agitated at a high rate (9,000 rpm, for about 15 min) to form an o/w emulsion and, at the same time, electrostatically adsorb calcium microparticles around oil droplets. Then, as an edible sticking agent, casein sodium is added thereto, followed by addition of citric acid under agitation at a low rate to insolubilize the casein. As a result, the calcium microparticles adsorbed around the oil droplets are stuck by the casein to form edible oil-containing calcium shells. The conditions of the above low rate agitation are at 3,000 rpm and for about 5 min. Subsequently, the resultant solution containing the calcium shells are, for example, centrifuged and dried to thereby obtain edible oil-containing calcium microparticles.

When organic calcium such as calcium lactate, calcium citrate or calcium gluconate is used as the calcium shell-forming material, an edible oil and a calcium salt powder are added to water and agitated at a high rate to form an o/w emulsion and, at the same time, electrostatically adsorb calcium microparticles around oil droplets. (At this time, one to several percent of the calcium salt is dissolved in water). Then, a phosphate such as dipotassium hydrogenphosphate is added thereto to make the pH to be on the alkali side, followed by agitation at a low rate. As a result, the calcium salt of an organic acid dissolved is precipitated as calcium phosphate and renders the calcium powder adsorbed around the oil droplets stuck, to thereby form calcium shells. The conditions for the above agitations are the same as employed when inorganic calcium was used. Subsequently, the solution containing the calcium shells are centrifuged and dried to thereby obtain edible oil-containing calcium shells.

When the thus obtained edible oil-containing calcium shells are placed in an alcohol and/or a polar solvent, agitated lightly, filtered and washed with a similar solvent, the edible oil contained inside the calcium shells or adhered to their surfaces is replaced with the polar solvent. Therefore, when the solvent is volatalized by drying, porous, hollow calcium shells are obtained which substantially consist of calcium or a calcium salt.

A big difference between the present invention and the invention disclosed in Japanese Unexamined Patent Publication No. 7-328416 filed previously by the present inventors resides in this point.

More specifically, by employing the above constitution, it has become possible to use as a core substance not only an oily or oil-soluble substance but also a water-soluble substance, suspension or microorganism that has been extremely difficult or impossible to enclose.

As the alcohol or the polar solvent to be replaced with the edible oil, various alcohols or solvents may be used, but ethanol is preferable since the core substance-containing calcium microparticles of the invention are intended for use mainly in foods and pharmaceutical products.

Among the hollow calcium shells of the above described types, those produced from milk calcium are high in raw material cost, but they are extremely small in particle size and absorbed very well in the body; those produced from inorganic calcium are not absorbed very well in the body, but they are low in material cost and excellent in thermal insulation; those produced from organic calcium are positioned almost at the middle of the above two in terms of cost and properties.

As the edible oil to be used in the present invention for preparing porous, hollow calcium shells, almost any edible oil may be used. However, as a result of various investigations taking into account of relationship with ethanol to be replaced with the oil, the inventors have found it preferable to use a medium-chain fatty acid ester readily soluble in ethanol, such as Panacete™ manufactured by NOF Corp.

By using the hollow calcium shells obtained by the above-described method, any substance can be enclosed as a core substance. Briefly, a desired substance is dissolved in an aqueous solvent or dispersed as microparticles; the hollow calcium shells described above are added to the solution or the dispersion; while agitating, the mixture is degassed by reducing the pressure with a vacuum pump; then, the pressure is returned to ambient pressure. As a result, the aqueous solution or suspension of the core substance enters into the hollow calcium shells since they are porous.

Preferably, the concentration of the solution or suspension of the core substance is high unless its viscosity becomes too high, because a higher concentration can render a higher content of the core substance in the calcium shells. As to the suspension, the size of suspending particles is preferably 10 $\mu$m or less. However, even suspending particles 20–30 $\mu$m in size can enter into the hollow calcium shells through pore voids present abundantly, as long as the particles have some elasticity. Although the liquid temperature in the pressure reducing step has no direct relationship with introduction of the core substance into the calcium shells, it is preferred that the liquid temperature be relatively high as long as the core substance is stable at that temperature, because a high liquid temperature improves the solubility of the core substance and thus the core substance of a higher concentration enters into the calcium shells. On the other hand, since the calcium shells can sufficiently stand a temperature up to 150° C., the liquid temperature does not affect them.

As to the volume ratio of the hollow calcium shells to the core substance-containing solution, usually the ratio is set at the hollow calcium shells:the core substance-containing solution=1:1. This ratio may be altered to 1:2–6. This ratio depends on the void ratio of the hollow calcium shells. According to the present invention, the void ratio ranges from approximately 60 to 95%.

The core substance-containing calcium microparticles of the invention can select various substances as a core substance depending on the purpose of use of the microparticles. For example, the following core substances and purposes may be enumerated.

(1) Table luxuries such as tea and coffee are enclosed in order to retain their taste and aroma for a long period of time.

(2) Seasonings such as soybean paste and soy sauce are enclosed to make them into powder in order to improve their storage life and to facilitate their transportation.

(3) Shrimp, crab or bonito flavor is enclosed in order to maintain the flavoring ability for a long period of time.

(4) Vitamins unstable against heat and light, such as vitamin C, are enclosed in order to stabilize them and to protect them from heating at the time of processing when they are used as a raw material for manufacturing food.

(5) Those substances which present a bitter taste, such as powder of Gymnema leaves or heme iron used as an additive to health food, are enclosed in order to mask the taste.

(6) Those substances which stimulate the gastric mucous membrane, such as aspirin, are enclosed in order to confer acid resistance (i.e. make an enteric formulation).

(7) Water-soluble antibiotics, such as penicillin, are enclosed in order to confer slow release property.

(8) Useful microorganisms, such as *Lactobaciillus bifidus* and yeast, are enclosed in order to protect them from gastric acid and to increase their survival.

Since the major component of the outer shell of the microparticles of the invention is calcium, the microparticles also serve as a calcium supplement.

After a core substance has been introduced into hollow calcium shells, they are dried to remove moisture. This drying may be performed with hot air of 80–120° C. if the core substance is stable against heat. In other cases, the drying is performed by freeze-drying. If it is necessary to increase the amount of core substance inside the hollow calcium shells, the shells after drying may be remixed with a solution or suspension of the core substance and then re-dried. These operations may be carried out repeatedly.

Introduction of a core substance into the hollow calcium shells by itself will produce some masking effect or protecting effect on the core substance. However, in order to make such effect sufficient, it is preferable to coat the core substance-containing calcium shells. The term "coat" used herein means to fill up voids in the porous calcium shells in order to prevent the core substance from leaking, and eventually to apply coating on the entire surface of the calcium shells. If the purpose is mere coating, various coating materials may be used as long as they are soluble in a hydrophilic solvent and edible. However, as a coating material to confer the special function as described above, the inventors have found that an edible biopolymer is preferable for the purpose.

The term "biopolymer" used herein means a high molecular substance derived from animals or plants. Most of such biopolymers form a gel. Specific examples include animal-derived biopolymers such as myosin (muscle protein); plant-derived biopolymers such as alginic acid, zein, mannan, carrageenan, soybean protein, dextrin, starch; and microorganism-derived biopolymers such as Cardran, xanthan gum.

These substances may be used alone for the purpose of masking a simple taste. It is also possible to use two or three of these substances in combination so that they are crosslinked to form a gel; thus, a property that could not be achieved by the use of one substance alone can be achieved. Examples of such crosslinking are given in Table 1 below.

TABLE 1

| Combination | Effects |
| --- | --- |
| Glucomannan + carrageenan | Prevention of the scattering of aroma; slow release property of drugs; temperature sensitivity (dissolution at a specific temp.) |
| Gelatin + carrageenan | pH sensitivity (dissolution at pH 8 or above); rise of melting point |
| Gelatin + sodium alginate | Rise of melting point; masking of taste |
| Casein sodium + chitosan | Inhibition of the volatilization of aroma; masking of taste |
| Konjak mannan + carrageenan | Slow release of aroma; masking of taste |

Since biopolymers undergo gelation, it is preferable to use them in the form of a sol at a concentration of 0.5–3.0%. However, gelatin is preferably used at a high concentration around 10–20% to produce good results.

The amount of use of the prepared sol is 2 to 50% by weight relative to the weight of the core substance-introduced calcium shells; 1 to 2% by weight is sufficient. The shells can be coated with the sol by mixing these two components and subsequently reducing the pressure according to conventional methods. Alternatively, the sol may be spray coated on the core substance-introduced shells suspending and rotating in air in a fluidized bed granulator. The sol is thus adsorbed on or adhered to the core substance-introduced calcium shells, and then dried for gelation. As a result, core substance-enclosing calcium microparticles can be obtained upon which a desired property or function is conferred.

Hereinbelow, the present invention will be described more specifically with reference to the following Examples.

EXAMPLE 1

Enclosure of Green Tea (a) Operations

One point zero (1.0) liter of water, 50 g of a medium-chain fatty acid ester (an edible oil) (manufactured by NOF Corp.; Panacete™) and 5 g of an emulsifier were placed in a beaker. While being kept at 80° C., the contents were agitated at 9,000 rpm for 5 min with a high speed homogenizer to prepare an o/w emulsion. To this emulsion, 200 g of calcium lactate powder was added and agitated. As a result, the powder was electrostatically adsorbed on the surface of oil droplets in the emulsion. Subsequently, 50 g of a saturated solution of potassium dihydrogenphosphate was added thereto and rapidly cooled under agitation to thereby stick the calcium lactate adhering around oil droplets. As a result, a suspension was prepared in which oil droplets were coated with porous calcium shells. Subsequently, this suspension was treated in a spray drier with the entrance temperature being 180° C. or below to thereby obtain 175 g of edible oil-containing calcium shells.

These calcium shells were put in 500 ml of ethanol solution and shaken for 1 to 2 hr to thereby replace the edible oil adhering to the inside and the surface of the shells with ethanol. Thereafter, the calcium shells were separated and washed with 500 ml of ethanol. As a result, almost the entire volume of the edible oil was replaced with ethanol. Subsequently, ethanol was evaporated by air-drying at 100° C. to obtain 110 g of porous, hollow calcium shells mainly composed of calcium lactate.

On the other hand, 50 g of high quality green tea was crushed to less than 100 mesh and added to 200 ml of 10% aqueous solution of α-cyclodextrin (product name: k-100; Ensuiko Sugar Refining Co., Ltd.) followed by mixing. Subsequently, 100 g of the hollow calcium lactate shells obtained above was added to the mixture. The air inside the calcium shells was vacuum sucked for 10 min while agitating the mixture. Thereafter, the pressure was returned to ambient pressure to thereby introduce the green tea suspension into the calcium shells. After the shells were freeze-dried by conventional methods, 80 ml of 10% aqueous gelatin solution at 50° C. was added thereto and air-dried at 70° C. while mixing. As a result, 125.6 g of green tea-enclosing calcium microparticles was obtained.

(b) Storage Test

The green tea-enclosing calcium microparticles obtained in (a) above and powder of high quality green tea (obtained by simply crushing a high quality green tea similar to the green tea enclosed) were stored for 6 months at ambient temperature in brown bottles. Immediately before the start of storage and 3 months and 6 months thereafter, a sample was taken from each bottle. Warm water was poured to the sample, and changes in color tone and aroma were examined.

The results are shown in Table 2 below. When green tea was enclosed in the calcium microparticles of the invention, both color tone and aroma were maintained stably even after 6 month storage; they were almost the same as those immediately after the production. In the control sample, color tone and aroma remarkably deteriorated after 3 month storage. After 6 month storage, a part of the control sample changed to brown, and most of its aroma was lost.

Hollow calcium shells which are suitable for use to enclose green tea are shells of a calcium salt of organic acid.

In this Example, calcium lactate was used. Similar results were obtained when other calcium salts of organic acid were used.

TABLE 2

| Test Sample | | Immediately before storing | After 3 months | After 6 months |
|---|---|---|---|---|
| Green tea powder (control) | Color | +++ | + | − |
| | Aroma | +++ | + | − |
| Green tea-enclosing microparticles | Color | ++ | ++ | +± |
| | Aroma | ++ | ++ | +± |

EXAMPLE 2
Enclosure of Bonito Flavor
(a) Operations

One point zero (1.0) liter of 0.5% aqueous solution of casein sodium and 128 g of a medium-chain fatty acid ester (an edible oil) (Panacete™ manufactured by NOF Corp.) were placed in a beaker and agitated at ambient temperature at 9,000 rpm for 15 min with a high speed homogenizer to prepare an o/w emulsion. To this emulsion, 100 g of milk calcium powder (manufactured in New Zealand) and 200 g of calcium carbonate powder (Porecal™ manufactured by Shiraishi Calcium) were added and agitated. As a result, calcium powder was electrostatically adsorbed on the surface of oil droplets in the emulsion. Subsequently, this mixture was spray-dried to thereby obtain 299.8 g of edible oil-containing calcium shells.

The edible oil adhering to the inside and the surface of the shells was replaced with ethanol in the same manner as in Example 1. Thereafter, the shells were dried to thereby obtain 207.7 g of porous, hollow calcium shells.

On the other hand, 50 ml of 20% aqueous solution of α-cyclodextrin (k-100; Ensuiko Sugar Refining Co., Ltd.) was added to 50 g of a bonito flavor and agitated at 4,000 rpm for 5 min to thereby enclose the flavor with the cyclodextrin. To this solution, 100 g of the hollow calcium shells obtained above was added. The resultant mixture was subjected to vacuum suction until air bubbles subsided. When bubbles became unobservable (after approximately 7 min suction), the pressure was returned to ambient pressure to introduce the flavor into hollow calcium shells.

After the calcium shells were dried, 2% aqueous solution of carrageenan/glucomannan (6:4) crosslinked material was prepared, and 25 ml of this solution was added to the flavor-enclosing calcium shells and mixed well. Subsequently, the mixture was rapidly freeze-dried to thereby obtain 112.7 g of bonito flavor-enclosing calcium microparticles.

(b) Storage Test

A functional test was conducted by 10 panelists on the above-described bonito flavor-enclosing calcium microparticles and bonito flavor powder (control) to compare the storage life of the aroma of the two samples. Briefly, 20 g of the bonito flavor-enclosing calcium microparticles obtained in (a) above and 10 g of non-enclosed bonito flavor powder as a control were placed in Petri dishes separately and allowed to stand at room temperature without any cover. Immediately after the start of the test, and 3 days, 10 days and 1 month thereafter, 100 ml of boiling water was added to the dish. At the time point when aroma was sensed, 100 ml of hot water was poured to dilute the solution. Dilution was repeated until no aroma could be sensed. The dilution ratio at this time point was taken as the threshold value of the flavor of the sample.

The results are shown in Table 3 below (threshold values are represented by dilution ratios). Immediately after the start of the test, the control sample had stronger aroma. However, with the passage of time, its aroma sharply reduced. The control sample which had been left for 3 to 5 days had little aroma even tested.

On the other hand, although the bonito flavor-enclosing calcium microparticles of the invention was weaker than the control in aroma immediately after the start of the test, the reduction of aroma with the passage of time was small. It was found that considerable aroma could still be sensed even after the microparticles had been left for 10 days.

The carrageenan/glucomannan crosslinked gel used in this Example as an enclosing agent is excellent in blocking aroma. Further, since this gel is dissolved in hot water, it is extremely convenient for use in the preparation of seasonings for instant soup.

TABLE 3

| Sample | Immediately after preparation | After 3 days | After 10 days |
|---|---|---|---|
| Flavor powder (control) | ×1200 | ×150 | not tested |
| Flavor-enclosing microparticles | ×700 | ×640 | ×480 |

EXAMPLE 3
Enclosure of Soybean Paste and Soy Sauce

One point zero (1.0) liter of 0.5% aqueous solution of casein sodium and 100 g of a medium-chain fatty acid ester (an edible oil) (Panacete™ manufactured by NOF Corp.) were placed in a beaker and agitated at ambient temperature at 9,000 rpm for 15 min with a high speed homogenizer to prepare an o/w emulsion. To this emulsion, 120 g of calcium carbonate powder (Porecal™ manufactured by Shiraishi Calcium) and 13 g of sodium carbonate were added in mixture and agitated. As a result, calcium powder was electrostatically adsorbed on the surface of oil droplets in the emulsion. Subsequently, this mixture was spray-dried to thereby obtain 166.6 g of edible oil-containing calcium microparticles.

These particles were treated with ethanol in the same manner as in Example 1, to thereby replace the edible oil adhering to the inside and the surface of the calcium shells with ethanol. Thereafter, the shells were dried to thereby obtain 91 g of porous, hollow calcium carbonate shells.

On the other hand, 50 ml of hot water was added to 50 g of soybean paste and mixed to prepare a soybean paste suspension. To this suspension, 70 g of the above hollow calcium shells was added and agitated under reduced pressure. Subsequently, the pressure was returned to ambient pressure to thereby introduce the soybean suspension into the calcium shells. Thereafter, the shells were air-dried at 80–100° C. to thereby obtain 75 g of soybean paste-containing calcium lumps.

These lumps can be easily crushed to yield dry soybean paste-containing calcium microparticles. Also, soy sauce can be processed likewise. By processing paste-type seasonings such as soybean paste or liquid-type seasonings such as soy sauce as described above, their storage life can be improved. Therefore, it is not necessarily required to further treat such seasoning-containing calcium microparticles with a biopolymer.

The above-mentioned seasoning processed by the method of the invention is easy to transport and store, and can be easily used for the purpose of seasoning. Besides, since the calcium shells are dissolved in the body, calcium can be supplied simultaneously.

EXAMPLE 4

Enclosure of Vitamin C (a) Operations

A saturated solution (about 35%) of vitamin C or a calcium salt thereof in hot water was prepared in advance. While agitating 200 ml of this solution with 100 g of the porous, hollow calcium carbonate shells obtained in the course of Example 3, the mixture was vacuum sucked for 10 min to remove the air contained inside the hollow calcium shell. Thereafter, the pressure was returned to ambient pressure to thereby introduce the saturated solution into hollow calcium shells. Then, the shells were vacuum dried at 60° C. to recrystallize vitamin C inside the shells. As a result, 156 g of vitamin C-containing porous calcium microparticles was obtained.

On the other hand, 1 g of chitosan was dispersed in 100 ml of water. Then, 1 g of lactic acid was added thereto to dissolve the chitosan. Thirty grams of this solution was added to 156 g of the above vitamin C-containing porous calcium microparticles. While the two components were mixed under agitation, vacuum suction was conducted to thereby coat the microparticles with chitosan. Subsequently, 50 g of 4% aqueous casein sodium solution was added and mixed under agitation. As a result, sodium in the casein sodium was separated; and casein was insolubilized to solidify the chitosan coating. The solid matters were separated therefrom and air-dried at 80–100° C. to thereby obtain 126 g of vitamin C-enclosing calcium microparticles.

(b) Thermal Resistance Test

To a raw material having the composition as described below, 2.0% by weight of vitamin C or 4.5% by weight of the above-mentioned vitamin C-enclosing calcium microparticles was added. The mixture was loaded into an extruder and treated with pressure and heat by conventional methods to obtain a pellet. Thus, a feed for cultured fishes (young yellowtail) was prepared.

| Composition: | Minced anchovy | 76.0 (% by weight) |
|---|---|---|
| | Gluten | 18.0 |
| | Vitamin mix | 3.2 (of which 1.2 is vitamin C) |
| | Mineral mix | 1.0 |
| | Corn oil | 1.8 |

Usually, some vitamins combined in fish feeds, such as vitamin C and β-carotene, undergo thermal degradation. When a raw material for feed is treated in an extruder as described above, it is reported that vitamin C is degraded and reduced up to approximately ½ to Then, the residual ratios of vitamin C in both the above pellet feeds were examined. In the control pellet in which vitamin C was combined without any processing, the residual ratio was 23.1%. In contrast, it was found that the residual ratio was 89.7% in the pellet in which the vitamin C-enclosing calcium microparticles were combined.

EXAMPLE 5

Enclosure of Aspirin (a) Operations

Eight hundred milliliters of 0.5% aqueous solution of casein sodium and 60 g of a medium-chain fatty acid ester (an edible oil) (Panacete™ manufactured by NOF Corp.) were placed in a beaker and agitated at ambient temperature at 9,000 rpm for 15 min with a high speed homogenizer to prepare an o/w emulsion. To this emulsion, 150 g of milk calcium powder (manufactured in New Zealand) was added and agitated. As a result, calcium powder was electrostatically adsorbed on the surface of oil droplets in the emulsion. Subsequently, this mixture was spray-dried to thereby obtain 147.0 g of edible oil-containing calcium shells.

The edible oil was replaced with ethanol in the same manner as in Example 1. Thereafter, the shells were dried to thereby obtain 98 g of porous, hollow milk calcium shells.

On the other hand, aspirin crystals were crushed into fine powder, 100 g of which was dispersed in 1.0 liter of cool water of 0–5° C. Subsequently, 50 g of the above hollow milk calcium shells was added thereto and vacuum sucked for 10 min while agitating to thereby withdraw air from the inside of the shells. Then, the pressure was returned to ambient pressure to thereby introduce the aspirin suspension into the calcium shells. Immediately thereafter, the shells were spray-dried to obtain 110 g of aspirin-containing calcium microparticles.

Further, 10% aqueous solution of gelatin/carrageenan (4:1) crosslinked material was prepared. Twenty grams of this solution was mixed with the above aspirin-containing calcium microparticles, agitated under reduced pressure and then air-dried at 80–100° C. to thereby obtain 95.2 g of aspirin-enclosing calcium microparticles.

(b) Disintegration Test

A disintegration test was conducted on the aspirin-enclosing calcium microparticles obtained in (a) above using the artificial gastric juice and intestinal juice stipulated in the Japanese Pharmacopoeia.

Briefly, to 100 ml each of artificial gastric juice and intestinal juice adjusted to 25° C., 5 g of the aspirin-enclosing calcium microparticles was added and agitated in every 15 min. One hour after the addition of the microparticles, aspirin elution ratio was determined.

As a result, the aspirin elution ratios of the microparticles of the invention were 1% or below in gastric juice (i.e. dissolved little) and 87% in intestinal juice. Thus, it was found that drugs liable to cause gastric disorder, such as aspirin, can be formulated into an enteric preparation by introducing them into calcium shells as described above and then coating the shells with a biopolymer having acid resistance.

EXAMPLE 6

Enclosure of Penicillin (a) Operations

One point zero (1.0) liter of water, 50 g of a medium-chain fatty acid ester (an edible oil) (Panacete™ manufactured by NOF Corp.) and 5 g of an emulsifier were placed in a beaker and agitated at 9,000 rpm for 10 min with a high speed homogenizer while maintaining the liquid temperature at 50° C., to thereby prepare an o/w emulsion. To this emulsion, 160 g of calcium citrate powder and 40 g of calcium gluconate were added and agitated. As a result, calcium powder (mainly calcium citrate) was electrostatically adsorbed on the surface of oil droplets in the emulsion. Subsequently, 20 ml of saturated solution of potassium dihydrogenphosphate was added thereto and cooled rapidly under agitation to thereby stick the calcium adhering around oil droplets. As a result, a suspension was prepared in which oil droplets are coated with porous calcium shells. Subsequently, the solid matters were separated by centrifugation, washed with water and then air-dried at 100° C. to thereby obtain 187.5 g of edible oil-containing calcium microparticles.

These particles were treated with ethanol and dried in the same manner as in Example 1 to obtain 140.1 g of porous calcium shells.

Subsequently, 20 g of potassium penicillin G was dissolved in 100 ml of warm water (50° C.). To this solution, 70 g of the above calcium shells were added and vacuum sucked for 10 min under agitation to withdraw air from the inside of the hollow calcium shells. Thereafter, the pressure was returned to ambient pressure to thereby introduce the aqueous solution of potassium penicillin G into the hollow calcium shells. Then, these shells were immediately freeze-dried to thereby obtain 87 g of potassium penicillin G-containing calcium microparticles.

On the other hand, 10% aqueous solution of glucomannan/carrageena n (5:1) crosslinked material was prepared, and 5 g, 10 g, 15 g and 20 g of this solution were placed in separate containers. To each of these containers, 15 g of the above potassium penicillin G-containing calcium microparticles was added and agitated under reduced pressure.

Subsequently, the resultant mixture was vacuum dried at 50° C. or below to thereby obtain 4 types of potassium penicillin G-enclosing calcium microparticles different in water-solubility.

(b) Test of Elution into Serum (in vitro Test)

The amount of eluted penicillin was determined as follows. One gram of each type of the potassium penicillin G-enclosing calcium microparticles was added to 100 ml of fresh bovine serum, and bioassay was conducted to examine the time course of penicillin elution using the cylinder plate method.

The results are shown in Table 4 below. The amount of penicillin eluted into serum decreased in inverse proportion to the amount of glucomannan/carrageenan crosslinked material added.

TABLE 4

| Amount of glucomannan/ carrageenan crosslinked | Penicillin G Elution (U/ml) | | | |
|---|---|---|---|---|
| material added (g) | 15 min | 30 min | 60 min | 75 min |
| 5 | 107 | 533 | 845 | 100 |
| 10 | 59 | 216 | 715 | 920 |
| 15 | 40 | 179 | 624 | 909 |
| 20 | >10 | 108 | 558 | 627 |

(c) Determination of Blood Level (in vivo Test)

One gram sample was taken from each of the 4 types of potassium penicillin G-enclosing calcium microparticles obtained in (a) and mixed to uniformity. A dispersion of these microparticles was administered intragastrically to 10 Donrhyu strain rats about 200 g in body weight compulsorily (5000 U/kg). Blood samples were collected at regular invervals, and the blood levels of potassium penicillin G were determined by bioassay. As a control, the same amount of potassium penicillin G without any processing was administered orally to 10 rats compulsorily. Then, the blood levels of these two groups was compared.

The results (average blood levels in each group) are shown in Table 5 below. When unprocessed penicillin G was administered, the Blood level reached the peak 60 min after the administration but it decreased to less than ½ of 0.5 μg/ml (which is considered to be the minimum effective concentration) 90 min after the administration. When the penicillin G-enclosing calcium microparticles of the invention were administered, a blood level above the minimum effective concentration was maintained for more than 90 min. Thus, it was found that slow release property is achieved by the microparticles of the invention.

TABLE 5

| | Blood Level of Penicillin G (μg/ml) | | |
|---|---|---|---|
| Test Sample | 30 min | 60 min | 90 min |
| Unprocessed Penicillin G | 0.57 | 0.91 | 0.23 |
| Penicillin G-Enclosing Microparticles | 0.49 | 0.88 | 0.75 |

EXAMPLE 7

Enclosure of Lactobacillus bifidus (a) Operations

Five hundred milliliters of 1.0% aqueous solution of casein sodium and 95 g of a medium-chain fatty acid ester (an edible oil) (Panacete™ manufactured by NOF Corp.) were placed in a beaker and agitated at ambient temperature at 9,000 rpm for 15 min with a high speed homogenizer to prepare an o/w emulsion. To this emulsion, 25 g of milk calcium powder (manufactured in New Zealand) and 100 g of calcium carbonate powder (Porecal™ manufactured by Shiraishi Calcium) were added and agitated. As a result, calcium powder was electrostatically adsorbed on the surface of oil droplets in the emulsion. Subsequently, this mixture was spray-dried to thereby obtain 155.4 g of edible oil-containing calcium microparticles.

These microparticles were treated with ethanol in the same manner as in Example 1 to replace the edible oil adhering to the inside and the surface of the calcium shells with ethanol. Thereafter, the shells were dried to thereby obtain 80.0 g of porous, hollow milk calcium shells.

On the other hand, 15 g of commercial freeze-dried powder of *L. bifidus* (viable cell count: $4 \times 10^8$/ml) was dispersed in 60 ml of the edible oil described above. To this dispersion, 80 g of the above hollow calcium shells were added and vacuum sucked for 10 min under agitation to withdraw air from the inside of the shells. Then, the pressure was returned to ambient pressure to thereby introduce the *L. bifidus* suspension into the hollow calcium shells.

Further, 10 g of the above-mentioned milk calcium and 5 g of casein sodium were dispersed in 50 ml of water. Twenty-five grams of this dispersion was added to the above hollow calcium shells, agitated and then immediately freeze-dried to thereby obtain 113.7 g of *L. bifidus*-enclosing calcium microparticles.

(b) Determination of Viable Cell Count

In order to examine the acid resistance of the thus obtained *L. bifidus*-enclosing calcium microparticles and commercial *L. bifidus* freeze-dried powder, viable cell counts were determined on both samples using the artificial gastric juice stipulated in the Japanese Pharmacopoeia.

Briefly, 5 g of the *L. bifidus*-enclosing calcium microparticles of the invention or 1 g of commercial *L. bifidus* freeze-dried powder was added to 100 ml of artificial gastric juice. Sampling was conducted over 90 minutes. The artificial gastric juice sample taken was neutralized to pH 7.0. Then, the viable cell count was determined by the *L. bifidus* culture method stipulated in 1993 Japanese Pharmacopoeia.

The results are shown in Table 6 below. While a large part of the commercial *L. bifidus* is killed by gastric acid when administered orally, it has become clear that death of *L. bifidus* is inhibited when this bacterium is enclosed with hollow calcium shells according to the method of the invention, because the shells prevent gastric acid from entering thereinto and the calcium neutralizes gastric acid.

TABLE 6

| Test Sample | Viable Cell Count (cells/ml) | | | | |
| --- | --- | --- | --- | --- | --- |
| | 0 min | 15 min | 30 min | 60 min | 90 min |
| Commercial L. bifidus powder | $1.4 \times 10^8$ | $3.8 \times 10^7$ | $4.5 \times 10^6$ | $1.6 \times 10^4$ | $2.2 \times 10^3$ |
| L. bifidus-enclosing microparticles | $0.9 \times 10^8$ | $0.2 \times 10^8$ | $7.7 \times 10^7$ | $5.3 \times 10^7$ | $9.8 \times 10^6$ |

EXAMPLE 8
Enclosure of Glutathione-Containing Yeast

One point zero (1.0) liter of water and 128 g of a medium-chain fatty acid ester (an edible oil) (Panacete™ manufactured by NOF Corp.) were placed in a beaker and agitated at 9,000 rpm for 10 min with a high speed homogenizer to thereby prepare an o/w emulsion. To this emulsion, 300 g of milk calcium powder (manufactured in New Zealand) was added and agitated. As a result, calcium powder was electrostatically adsorbed on the surface of oil droplets in the emulsion. Subsequently, 20 ml of 0.3% sodium alginate solution was added thereto and agitated at 2,000 rpm for 5 min. Immediately thereafter, the resultant mixture was spray-dried to thereby obtain 342.4 g of edible oil-containing calcium shells.

These shells were treated with ethanol in the same manner as in Example 1 to replace the edible oil adhering to the inside and the surface of the calcium shells with ethanol. Then, the shells were dried to thereby obtain 213.0 g of hollow calcium shells.

On the other hand, glutathione-containing yeast powder (glutathione content: 10%; manufactured by Kohjin) was dissolved in water to prepare 15% glutathione-containing yeast solution. To this solution (250 g), 200 g of the above hollow calcium shells and 25 g of casein sodium were added and agitated under reduced pressure. Then, the pressure was returned to ambient pressure to introduce the glutathione solution into the calcium shells.

Immediately thereafter, the resultant mixture was spray-dried to thereby obtain 210.0 g of glutathione-containing yeast-enclosing calcium microparticles. When the thus obtained microparticles were licked, the taste peculiar to glutathione-containing yeast was reduced. Also, the smell was reduced.

EXAMPLE 9
Enclosure of Magnesium Chloride

Five hundred milliliters of 1.0% aqueous solution of casein sodium and 105 g of a medium-chain fatty acid ester (an edible oil) (Panacete™ manufactured by NOF Corp.) were placed in a beaker and agitated at ambient temperature at 9,000 rpm for 15 min with a high speed homogenizer to prepare an o/w emulsion. To this emulsion, 43 g of milk calcium powder (manufactured in New Zealand) and 100 g of calcium carbonate powder (Porecal™ manufactured by Shiraishi Calcium) were added and agitated. As a result, calcium powder was electrostatically adsorbed on the surface of oil droplets in the emulsion. Immediately thereafter, this mixture was spray-dried to thereby obtain 198 g of edible oil-containing calcium shells.

These shells were treated with ethanol in the same manner as in Example 1 to replace the edible oil adhering to the inside and the surface of the calcium shells with ethanol. Then, the shells were dried to obtain hollow calcium shells.

Forty grams of the hollow calcium shells and 10 g of casein sodium were mixed. To this mixture, 100 g of 50% magnesium chloride solution was added and agitated at 4,500 rpm for 5 min. This mixture was placed under reduced pressure, and then returned to ambient pressure to thereby introduce magnesium chloride into the calcium shells.

Subsequently, lactose and egg white powder were mixed at a ratio of 3:1, and 5% solution of this powder was prepared. Two hundred grams of this solution was added to the above mixture containing magnesium chloride solution and calcium shells and agitated. Then, the resultant mixture was immediately spray-dried to thereby obtain 80.0 g of magnesium chloride-enclosing calcium microparticles.

When the resultant microparticles were licked, the bitter taste of magnesium chloride was reduced. No deliquescence was observed even after the microparticles had been left at room temperature for more than one month.

EXAMPLE 10
Enclosure of Vitamin E

One point zero (1.0) liter of 0.5% aqueous solution of casein sodium and 182 g of a medium-chain fatty acid ester (an edible oil) (Panacete™ manufactured by NOF Corp.) were placed in a beaker and agitated at ambient temperature at 9,000 rpm for 15 min with a high speed homogenizer to prepare an o/w emulsion. To this emulsion, 210 g of milk calcium powder (manufactured in New Zealand) and 109 g of calcium carbonate powder (Porecal™ manufactured by Shiraishi Calcium) were added and agitated. As a result, calcium powder was electrostatically adsorbed on the surface of oil droplets in the emulsion. Then, this mixture was spray-dried to thereby obtain 375.7 g of edible oil-containing calcium shells.

Subsequently, the edible oil adhering to the inside and the surface of the calcium shells was replaced with ethanol in the same manner as in Example 1. Then, the shells were dried to thereby obtain 191.3 g of porous, hollow calcium shells.

Vitamin E (55.4 g) and Panacete™ (100 g) were mixed to prepare a vitamin E oil, which was then agitated with 190 g of the porous, hollow calcium shells under reduced pressure to allow adsorption of the vitamin E oil on the shells.

On the other hand, 1.36 g of glucomannan, 12.4 g of carrageenan, 4.1 g of gerangum and 6.9 g of locust bean gum were added to 800 g of water, which was then heated to 80° C. and agitated at 4,000 rpm for 5 min while retaining that temperature to prepare a solution of sticking agent. This solution was added to the above-mentioned vitamin E-containing calcium microparticles and agitated for 5 min. Thereafter, the resultant mixture was treated in a spray drier in which the entrance temperature was set at 180° C., to thereby obtain 314.6 g of vitamin E-enclosing calcium microparticles. These microparticles were placed in constant temperature water of 85° C. and left for 10 min. However, no leakage of oil component (vitamin E) or polymerization was observed.

EXAMPLE 11
Enclosure of β-Carotene

One point zero (1.0) liter of 0.5% aqueous solution of casein sodium and 200 g of a medium-chain fatty acid ester (an edible oil) (Panacete™ manufactured by NOF Corp.) were placed in a beaker and agitated at ambient temperature at 9,000 rpm for 15 min with a high speed homogenizer to prepare an o/w emulsion. To this emulsion, 244 g of calcium carbonate powder (Porecal™ manufactured by Shiraishi Calcium) was added and agitated. As a result, calcium powder was electrostatically adsorbed on the surface of oil droplets in the emulsion. Then, this mixture was spray-dried to thereby obtain 333 g of edible oil-containing calcium shell microparticles.

These microparticles were treated with ethanol in the same manner as in Example 1 to replace the edible oil adhering to the inside and the surface of the calcium shells with ethanol. Then, the shells were dried to thereby obtain 133.2 g of porous, hollow calcium carbonate shells.

To these porous, hollow calcium carbonate shells (130 g), β-carotene oil (containing β-carotene by 30%) (106 g) was added and agitated under reduced pressure to allow adsorption. Further, 10% aqueous solution of gelatin/carrageenan (4:1) crosslinked material was prepared. Twenty-five grams of this solution was added to the above mixture containing calcium carbonate shells and agitated. Subsequently, the resultant mixture was air-dried at 100° C. to thereby obtain 188.6 g of β-carotene-enclosing calcium microparticles. These microparticles were left under UV light for 24 hours, and the time course of the color was observed. As a result, no fading was recognized. It was found that the calcium shells protect β-carotene from oxidation.

Oily, physiologically active substances such as capsaicin can be enclosed and stabilized in the same manner.

What is claimed is:

1. A method for producing core substance-containing microparticles, comprising:
    a) producing, by electrostatic attraction, micro calcium-containing shells on the surfaces of droplets of an emulsion comprising oil;
    b) replacing the oil with one or more alcohols and/or polar solvents,
    c) drying the resultant microparticles to thereby prepare porous, hollow calcium-containing shells and
    d) introducing a core substance into the hollow shells.

2. The method for producing core substance-containing microparticles according to claim 1, wherein the emulsion further comprises an aqueous phase.

3. A method for producing core substance-containing microparticles, comprising:
    a) forming an emulsion comprising oil droplets;
    b) inducing an electrostatic potential on the surfaces of the emulsion droplets;
    c) forming a solid shell of calcium-containing materials by electrostatic attraction on the surfaces of the emulsion droplets;
    d) separating solid materials from the resultant mixture by centrifugation or filtration and drying the solid materials to thereby generate calcium-containing shells containing oil;
    e) replacing the oil contained in the calcium-containing shells with one or more alcohols and/or polar solvents and drying the shells to thereby generate hollow calcium-containing shells;
    f) adding the hollow calcium-containing shells to a core substance solution or suspension and introducing the core substance into the hollow shells under reduced pressure; and
    g) drying the resultant core substance-filled shells.

4. The method for producing core substance-containing microparticles according to claim 3, wherein the emulsion further comprises an aqueous phase.

5. The method for producing core substance-containing microparticles according to claim 1 or claim 3, wherein the method further comprises coating the core substance-containing shells with a biopolymer.

6. The method for producing core substance-containing microparticles according to claim 5, wherein the biopolymer comprises a biopolymer chosen from gelatin, casein, milk protein, myosin, carrageenan, alginic acid, chitosan and mannan.

7. The method for producing core substance-containing microparticles according to claim 1 or claim 3, wherein the calcium-containing material for shell formation comprises a material chosen from milk calcium, inorganic calcium salts and organic calcium salts.

8. The method for producing core substance-containing microparticles according to claim 7, wherein a casein salt and an organic acid are added to the calcium containing material as shell-forming material aids when said material is an inorganic calcium salt.

9. The method for producing core substance-containing microparticles according to claim 7, wherein a phosphate is added to the calcium-containing material for shell formation as a shell-forming aid when said material is an organic calcium salt.

10. The method for producing core substance-containing microparticles according to claim 1 or claim 3, wherein the oil comprises a medium-chain fatty acid ester and at least one of the substances replacing the oil is ethanol.

11. The method for producing core substance-containing microparticles according to claim 1 or claim 3, wherein the core substance comprises at least one core substance chosen from table luxuries, seasonings, water-soluble flavoring agents, vitamins, drugs, antibiotics, physiologically active substances and microorganisms.

* * * * *